United States Patent
Jackson et al.

(10) Patent No.: US 10,667,958 B2
(45) Date of Patent: Jun. 2, 2020

(54) ACQUISITION DISTRIBUTION LAMINATE

(71) Applicant: Kimberly-Clark Worldwide, Inc., Neenah, WI (US)

(72) Inventors: David M. Jackson, Alpharetta, GA (US); Roger Bradshaw Quincy, III, Roswell, GA (US); April Montoya Vaverka, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 140 days.

(21) Appl. No.: 15/778,842

(22) PCT Filed: Dec. 2, 2015

(86) PCT No.: PCT/US2015/063336
§ 371 (c)(1),
(2) Date: May 24, 2018

(87) PCT Pub. No.: WO2017/095399
PCT Pub. Date: Jun. 8, 2017

(65) Prior Publication Data
US 2019/0247238 A1    Aug. 15, 2019

(51) Int. Cl.
*A61F 13/15*    (2006.01)
*A61F 13/537*   (2006.01)
(Continued)

(52) U.S. Cl.
CPC ...... *A61F 13/15203* (2013.01); *A61F 13/535* (2013.01); *A61F 13/537* (2013.01);
(Continued)

(58) Field of Classification Search
CPC .. B32B 5/022; B32B 5/26; B32B 7/02; B32B 7/04; B32B 5/08; B32B 2307/718;
(Continued)

(56) References Cited

U.S. PATENT DOCUMENTS 3,849,241 A    11/1974 Butin
4,100,324 A    7/1978 Anderson
(Continued)

FOREIGN PATENT DOCUMENTS

EP    2901993 A1    8/2015
WO    WO9516425 A2    6/1995
(Continued)

*Primary Examiner* — Michael C Miggins
(74) *Attorney, Agent, or Firm* — Kimberly-Clark Worldwide, Inc.

(57) ABSTRACT

The present invention relates to a nonwoven acquisition distribution layer comprising: a) layered carded webs wherein the first layer comprises a carded web with high denier fibers wherein the denier is greater than about 5 d and a second layer comprising a carded web with low denier fibers wherein the denier is less than about 5 d and is positioned just below and in direct contact with the first layer; and b) a deflection layer comprising a fibrous nonwoven web wherein the fibrous nonwoven web has at least one component comprising meltblown, said meltblown having a basis weight of from about 15 gsm to about 50 gsm and having an air permeability of from about 45 ft³/min/ft² to about 350 ft³/min/ft²; and wherein the deflection layer is positioned just below and in direct contact with said second layer of said layered carded web.

7 Claims, 6 Drawing Sheets

(51) Int. Cl.
| | |
|---|---|
| *B32B 5/02* | (2006.01) |
| *B32B 5/26* | (2006.01) |
| *B32B 7/02* | (2019.01) |
| *B32B 7/04* | (2019.01) |
| *B32B 5/08* | (2006.01) |
| *A61F 13/535* | (2006.01) |
| *A61F 13/538* | (2006.01) |
| *A61F 13/53* | (2006.01) |

(52) U.S. Cl.
CPC ............ *A61F 13/538* (2013.01); *B32B 5/022* (2013.01); *B32B 5/08* (2013.01); *B32B 5/26* (2013.01); *B32B 7/02* (2013.01); *B32B 7/04* (2013.01); *A61F 2013/15406* (2013.01); *A61F 2013/15447* (2013.01); *A61F 2013/15552* (2013.01); *A61F 2013/530226* (2013.01); *A61F 2013/530233* (2013.01); *B32B 2250/03* (2013.01); *B32B 2250/05* (2013.01); *B32B 2250/20* (2013.01); *B32B 2262/0253* (2013.01); *B32B 2262/0284* (2013.01); *B32B 2262/067* (2013.01); *B32B 2262/12* (2013.01); *B32B 2307/718* (2013.01); *B32B 2307/724* (2013.01); *B32B 2307/726* (2013.01); *B32B 2307/728* (2013.01); *B32B 2535/00* (2013.01); *B32B 2555/02* (2013.01)

(58) Field of Classification Search
CPC ...... B32B 2307/724; B32B 2262/0253; B32B 2262/12; B32B 2250/20; B32B 2307/728; B32B 2555/02; B32B 2307/726; B32B 2262/0284; B32B 2535/00; B32B 2250/03; B32B 2262/067; B32B 2250/05; A61F 13/15203; A61F 13/537; A61F 13/535; A61F 13/538; A61F 2013/15406; A61F 2013/15447; A61F 2013/15552; A61F 2013/530226; A61F 2013/530233
See application file for complete search history.

(56) References Cited

U.S. PATENT DOCUMENTS

| | | |
|---|---|---|
| 4,372,312 A | 2/1983 | Fendler |
| 4,578,070 A | 3/1986 | Holtman |
| 4,681,577 A | 7/1987 | Stern |
| 4,704,116 A | 11/1987 | Enloe |
| 4,789,592 A | 12/1988 | Taniguchi |
| 4,795,668 A | 1/1989 | Krueger |
| 4,798,603 A | 1/1989 | Meyer |
| 4,886,512 A | 12/1989 | Damico |
| 4,908,026 A | 3/1990 | Sukiennik |
| 4,940,464 A | 7/1990 | Van Gompel |
| 5,057,368 A | 10/1991 | Largman |
| 5,069,970 A | 12/1991 | Largman |
| 5,108,820 A | 4/1992 | Kaneko |
| 5,162,074 A | 11/1992 | Hills |
| 5,192,606 A | 3/1993 | Proxmire |
| 5,257,982 A | 11/1993 | Cohen |
| 5,277,976 A | 1/1994 | Hogle |
| 5,336,552 A | 8/1994 | Strack |
| 5,350,624 A | 9/1994 | Georger |
| 5,364,382 A | 11/1994 | Latimer |
| 5,382,400 A | 1/1995 | Pike |
| 5,399,219 A | 3/1995 | Roessler |
| 5,466,410 A | 11/1995 | Hills |
| 5,508,102 A | 4/1996 | Georger |
| 5,540,796 A | 7/1996 | Fries |
| 5,558,659 A | 9/1996 | Sherrod |
| 5,595,618 A | 1/1997 | Fries |
| 5,614,295 A | 3/1997 | Quincy |
| 5,649,916 A | 7/1997 | DiPalma |
| 5,702,377 A | 12/1997 | Collier |
| 5,817,394 A | 10/1998 | Alikhan |
| 5,820,973 A | 10/1998 | Dodge |
| 5,853,402 A | 12/1998 | Faulks |
| 5,931,823 A | 8/1999 | Stokes |
| 5,989,688 A | 11/1999 | Barge |
| 6,060,638 A | 5/2000 | Paul |
| 6,110,158 A | 8/2000 | Kielpikowski |
| 6,127,595 A | 10/2000 | Makoui |
| 6,150,002 A | 11/2000 | Varona |
| 6,177,605 B1 | 1/2001 | Trombetta |
| 6,200,669 B1 | 3/2001 | Marmon |
| 6,511,465 B1 | 1/2003 | Freiburger |
| 6,608,236 B1 | 8/2003 | Burnes |
| 6,663,611 B2 | 12/2003 | Blaney |
| 6,689,242 B2 | 2/2004 | Bodaghi |
| 6,706,945 B1 | 3/2004 | Melius |
| 6,888,044 B2 | 5/2005 | Fell |
| 6,890,622 B2 | 5/2005 | Adam |
| 7,189,888 B2 | 3/2007 | Wang |
| 7,938,813 B2 | 5/2011 | Wang |
| 8,343,127 B1 | 1/2013 | Dimitrijevs |
| 8,618,351 B2 | 12/2013 | Di Girolamo |
| 2003/0118764 A1 | 6/2003 | Adams |
| 2003/0120249 A1 | 6/2003 | Wulz |
| 2003/0200991 A1 | 10/2003 | Keck |
| 2004/0060112 A1 | 4/2004 | Fell |
| 2004/0102750 A1 | 5/2004 | Jameson |
| 2004/0176733 A1 | 9/2004 | Glaug |
| 2005/0054255 A1 | 3/2005 | Morman |
| 2005/0059941 A1 | 3/2005 | Baldwin |
| 2012/0053547 A1 | 3/2012 | Schroeder |
| 2014/0276510 A1 | 9/2014 | Ducker |

FOREIGN PATENT DOCUMENTS

| | | | |
|---|---|---|---|
| WO | WO0143968 | A1 | 6/2001 |
| WO | WO17095399 | A1 | 6/2017 |

FIG. 6D ADL "C" (AP=51)

FIG. 6C ADL "B" (AP=78)

FIG. 6B ADL "A" (AP=122)

FIG. 6A Standard

FIG. 7

ACQUISITION DISTRIBUTION LAMINATE

FIELD OF THE INVENTION

The present invention relates to an improved acquisition distribution laminate that comprises layered carded webs and a deflection layer comprising a meltblown component which provides improved fluid intake, distribution, and transfer to an underlying absorbent core, especially cores with high levels of superabsorbent material.

BACKGROUND OF THE INVENTION

Personal care products such as absorbent articles including diapers, training pants, feminine hygiene products (such as sanitary napkins), incontinence articles, and the like are designed to absorb and contain body exudates and are generally single-use or disposable items which are discarded after a relatively short period of time. Such products usually are placed against or in proximity to the wearer's body to absorb and contain the various exudates discharged from the body. All of these products typically include a liquid permeable bodyside liner or cover, a liquid impermeable outer cover or backsheet, and an absorbent structure disposed between the bodyside liner and outer cover. The absorbent structure may include an acquisition distribution layer (ADL) positioned between a bodyside liner and an absorbent core.

Desirably, personal care absorbent products exhibit low leakage from the product and a dry feel for the wearer. It has been found that urination can occur at rates as high as 15 to 20 ml/sec and at velocities as high as 280 ml/sec. An absorbent article, such as a diaper or incontinence article, may fail by leaking from the leg, front or back waist areas. The inability for an absorbent article to rapidly uptake liquid can also result in excessive pooling of liquid on the body-facing surface of the bodyside liner before the liquid is taken up by the absorbent article. Such pooled liquid can wet the wearer's skin and can leak from leg or waist openings of the absorbent article, causing discomfort, potential skin health issues, as well as soiling of the clothing or bedding of the wearer.

Leakage and pooling can result from a variety of performance deficiencies due to the design structure of the product or materials used within the product. One cause of such problem is an insufficient rate of liquid intake into the absorbent core, which functions to absorb and retain body exudates. Another is that the products resulting are bulky and uncomfortable and are not used efficiently. In many instances, substantial portions of the absorbent layer are not used at all reducing the efficiency of the absorbent system. The liquid intake of a given absorbent article, therefore, and particularly the bodyside liner and ADL materials used, must meet or exceed the expected liquid delivery rates into the absorbent article.

Thus, there is a need to overcome the foregoing issues by improving the ADL which should have fast intake of fluid, the ability to distribute fluid throughout the majority of the material, and be able to quickly transfer the fluid to the underlying absorbent core. Fast intake and good distribution helps pull the fluid away from the body side liner for enhanced skin dryness and helps to utilize more of the underlying absorbent core to attain a more efficient and effective absorbent system. The ADL should function as a temporary reservoir to help contain fluid surges and efficiently and effectively drive the fluid into the majority of the core.

SUMMARY OF THE INVENTION

The present invention relates to a nonwoven acquisition distribution layer comprising: a) layered carded webs having at least a first layer and a second layer; and b) a deflection layer; wherein said first layer of said layered carded web comprises a carded web with high denier fibers wherein the denier is greater than about 5 d and a second layer of said layered carded web comprising a carded web with low denier fibers wherein the denier is less than about 5 d and is positioned just below and in direct contact with said first layer; and wherein said deflection layer comprises a fibrous nonwoven web wherein the fibrous nonwoven web has at least one component comprising meltblown, said meltblown having a basis weight of from about 15 gsm to about 50 gsm and having an air permeability of from about 45 ft$^3$/min/ft$^2$ to about 350 ft$^3$/min/ft$^2$; and wherein the deflection layer is positioned just below and in direct contact with said second layer of said layered carded web.

BRIEF DESCRIPTION OF THE DRAWINGS

A full and enabling disclosure of the present invention is set forth more particularly in the remainder of the specification, including reference to the accompanying figures, in which.

DETAILED DESCRIPTION OF THE INVENTION

While the specification concludes with the claims particularly pointing out and distinctly claiming the invention, it is believed that the present invention will be better understood from the following description.

All percentages, parts and ratios are based upon the total weight of the compositions of the present invention, unless otherwise specified. All such weights as they pertain to listed ingredients are based on the active level and, therefore; do not include solvents or by-products that may be included in commercially available materials, unless otherwise specified. The term "weight percent" may be denoted as "wt. %" herein. Except where specific examples of actual measured values are presented, numerical values referred to herein should be considered to be qualified by the word "about".

"Absorbent personal care product" or "absorbent article" as used herein includes, but is not limited to, absorbent articles such as diapers, training pants, absorbent underpants, adult incontinence products, feminine hygiene products and the like.

The term "carded web" or "bonded carded web" refers to webs that are made from staple fibers which are sent through a combing or carding unit, which separates or breaks apart and aligns the staple fibers in the machine direction to form a generally machine direction-oriented fibrous nonwoven web. Such fibers are usually purchased in bales which are placed in an opener/blender or picker which separates the fibers prior to the carding unit. Once the web is formed, it then can be bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using conjugate staple fibers, is through-air bonding. The carded web could also be positioned as layers and remained unbonded.

As used herein, "coform" refers to a process in which at least one meltblown diehead is arranged near a chute through which other materials are added to the web while it is forming. Such other materials may be pulp, superabsorbent particles, cellulose or staple fibers, for example. Coform processes are generally described in U.S. Pat. No. 4,100,324 to Anderson et al. Webs produced by the coform process are generally referred to as "coform materials" or "coform webs".

"Conjugate fibers" refers to fibers which have been formed from at least two polymer sources extruded from separate extruders but spun together to form one fiber. Conjugate fibers are also sometimes referred to as multicomponent or bicomponent fibers ("bico"). The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al, U.S. Pat. No. 5,336,552 to Strack et al and U.S. Pat. No. 5,382,400 to Pike et al.

As used herein "disposable absorbent article" refers to articles which absorb and contain body exudates and are intended to be discarded after a limited period of use (i.e., they are not intended to be laundered or otherwise restored for reuse). The articles can be placed against or in proximity to the body of the wearer to absorb and contain various exudates discharged from the body.

The term "liquid" is used herein with its customary meaning. As a practical matter, the liquid most often will be an aqueous liquid. When the web of the present invention is employed in an absorbent product, the liquid typically will be bodily excrement, such as urine, blood, menses, serum, and the like.

As used herein, the term "machine direction" or "MD" means a direction which is essentially parallel with the motion of a web through the web-forming, e.g., meltblowing, apparatus as the web is formed; i.e., a direction which is parallel with the direction of the forming wire upon which the web is formed. The MD is usually found along the length direction of the material as shown in FIGS. 1 & 2.

The term "cross direction" or "CD" is used herein to mean a direction which is the cross machine direction, i.e., a direction which is perpendicular to the machine direction. The CD is usually found along the width direction of the material as shown in FIG. 1.

Figure 1:
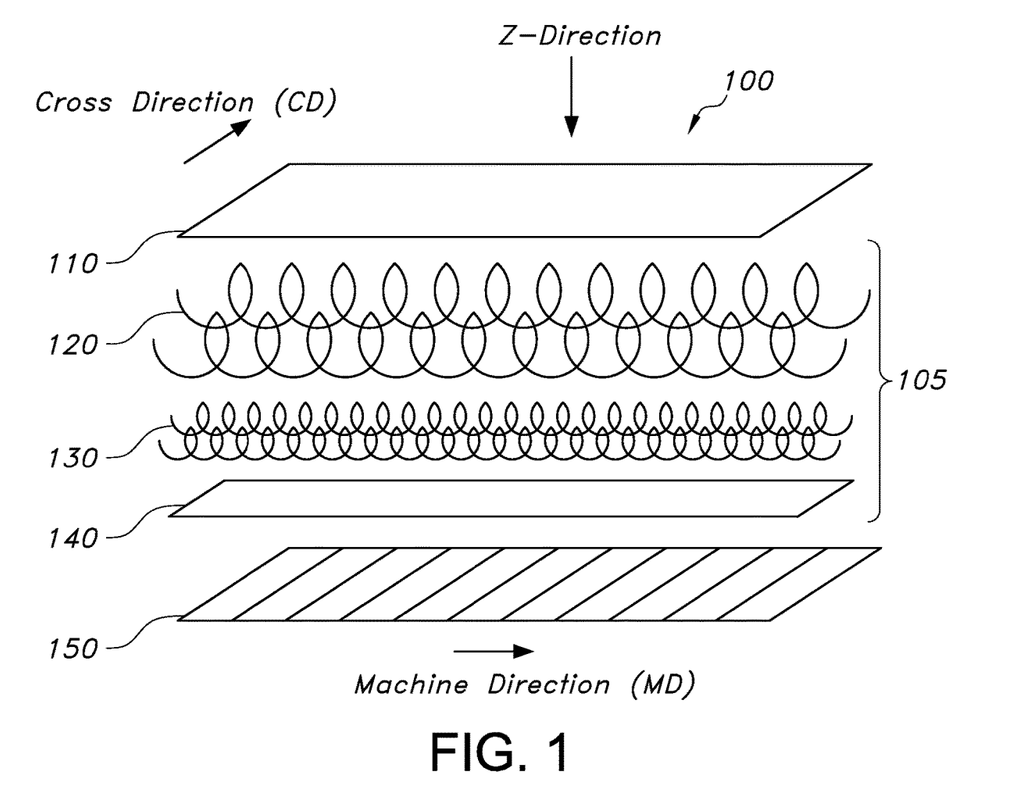
FIG. 1 is an exploded view of an absorbent system wherein the improved ADL of the present invention is shown.
Figure 2:
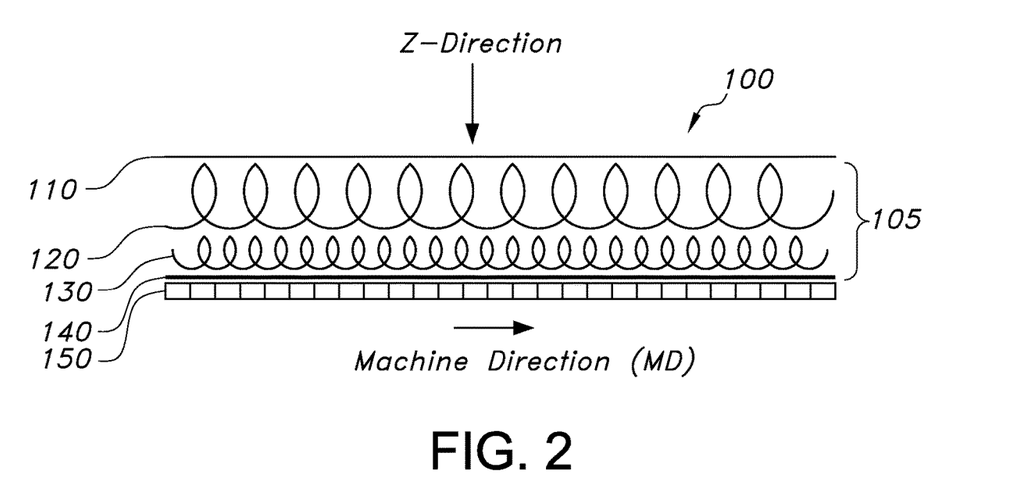
FIG. 2 is a cross-sectional view of an absorbent system wherein the improved ADL system of the present invention is shown.

The term "Z-Direction" refers to the downward direction of the material as shown in FIGS. 1 & 2.

"Meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to a microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin. Meltblown fibers are microfibers which may be continuous or discontinuous, are generally smaller than 10 microns in average diameter, and are generally tacky when deposited onto a collecting surface.

As used herein the term "nonwoven web" generally refers to a web having a structure of individual fibers or threads which are interlaid, but not in an identifiable manner as in a knitted fabric. Examples of nonwoven fabrics or webs include, but are not limited to, meltblown webs, spunbond webs, bonded carded webs, airlaid webs, coform webs, hydraulically entangled webs, and the like.

The use of any trademarks herein has been noted with CAPITALIZATION of the word wherever it appears to acknowledge and respect the proprietary nature held by the owners of the mark. The word is followed by the generic terminology only wherever it appears for the first time herein.

Carded web or airlaid material is a typical material usually used as a homogeneous distribution of fibers in an ADL. Although effective, these materials may possess limitations in providing all of the necessary functions desired in an absorbent product, i.e. fast intake, complete distribution, and transfer of fluid. To improve fluid intake, distribution, and transfer, dual or multi-layer laminate ADL structures are now presented that combine a non-homogeneous variety of gradients of carded webs in combination with a deflection layer comprising a fibrous nonwoven web wherein the fibrous nonwoven web comprises a meltblown component. The present ADL is more effective for products that contain absorbent cores, particularly those with higher levels of superabsorbent material (SAM), for example, greater than 50% superabsorbent material and provides better options for pulpless absorbent cores.

As shown in FIG. 1, an exploded view of an enhanced absorbent system (100) using the ADL of the present invention (105) shows that carded webs have been produced with a varying permeability gradient by using a large denier fiber composition layer (120) which, abuts or faces the body side liner (110). A small or smaller denier fiber composition layer (130) is then used directly below the large denier fiber composition layer (120). A deflection layer comprising a meltblown component (140) is then formed adjacent to the small denier fiber layer (130) preferably such that the deflection layer (140) also abuts or faces the absorbent core (150). This improved ADL system (105) enhances the permeability gradient for faster fluid intake in both the Z-direction (down) as well as promoting better fluid distribution in the MD prior to the fluid transfer into the underlying absorbent core (150).

The present invention provides for an improved ADL with enhanced fluid intake and distribution as well as more fluid transfer to the underlying absorbent core. It is especially useful to address "low-load" leakage or leakage in an absorbent article such as a diaper or incontinence article where the amount of liquid at insult is not at a level where leakage would be anticipated to occur based on the fluid capacity of the absorbent core. "Low-load" leakage is best explained through the following summary and example.

The approximate fluid capacity of an absorbent article based on the absorbent core can be determined by the composition of the absorbent core. For example, the amount of fluff pulp in the absorbent core might be expected to absorb about 8 g of fluid per gram of fluff pulp. Likewise, the amount of the superabsorbent in the absorbent core might be expected to absorb about 30 g of fluid per gram of superabsorbent. Thus, an absorbent article with an absorbent core that contains 10 g of fluff pulp and 10 g of superabsorbent would have a fluid capacity of about 380 g. An absorbent article with such an absorbent core would be characterized as experiencing "low-load" leakage if leakage occurred after liquid insults that delivered a total volume of about 150 g or less. The present invention, however, addresses this and other leakage issues with the present compositional structure.

The present invention utilizes a deflection layer which is a layer of a fibrous nonwoven web comprising a meltblown component in combination with a non-homogeneous and distinct gradient of layered carded webs to influence the amount of fluid spreading (MD distribution) and the amount transferred to the absorbent core (Z-direction distribution) such that the fluid is forced to spread to a larger extent and in a more uniform pattern. Furthermore, the enhanced fluid spreading results in better fluid transfer to the underlying absorbent core such that about twice as much fluid is able to be transferred to the absorbent core. Additionally, there is little to no rewet and no concentrated or localized wet spot area since there is an enhanced ability for the fluid to better distribute in the MD-direction. More fluid in the absorbent core results in improved skin dryness since less fluid will be present in the materials closer to the skin of the user. When evaluating the fluid retained in the present invention ADL versus a standard, the present invention has an approximate 10% improvement in the ADL layer and an approximate 50% increase in the absorbent core layer. For clarity, the "standard" ADL used as a comparative herein is a surge material comprising a homogeneous blend of fibers (35% 6 d PE/PP bico, 35% 1.5 d PE/PP Bico, 30% 6 d PET). The present ADL will greatly increase a feeling of dryness and an overall enhancement within an absorbent personal care product. Such improvement is explained in the following context.

ADL layers are provided within absorbent systems to quickly accept the incoming insult and either absorb, hold, channel or otherwise manage the liquid so that it does not leak outside of the absorbent article. The ADL layer may also be referred to as an intake layer, transfer layer, transport layer, surge layer, and the like. An ADL material must typically be capable of handling an incoming insult of between about 60 cc and 100 cc at an insult volumetric flow rate of from about 5 ml/sec to about 20 ml/sec. Absorbent core materials must absorb the insult quickly and efficiently by pulling the liquid from the ADL layer and absorbing the liquid without significant blocking of penetration of liquid further into the absorbent layer. Typical absorbent core materials are often high rate superabsorbent materials such as blends of polyacrylate superabsorbent and fluff. These materials are known for rapidly absorbing and holding liquid.

Bonded Carded Web

As shown in FIGS. 1 &2, the ADL of the present invention consists of at least two layers of a non-homogeneous blend of fibers, in particular a blend of large denier fibers as a body-facing side, first, top layer, and a second layer of small denier fibers positioned directly below and adjacent to the top layer, facing the absorbent core. This structure was achieved by carding a first layer of large denier fibers followed by a second layer of small denier fiber. Each of these layers may be lightly bonded by any bonding means such as a through air drier and allowed to wind up as separate rolls of fabric. The two layers may then be wound together and bonded together by passing through the air dryer. This gradient structure allows liquid to pass through rapidly upon insult in the open and more porous body side layer comprising the large denier fibers. Again, other conventional methods of bonding the layers together may be used and more than two layers may be used within the present invention. Also, the layers may be positioned as stated without bonding the layers together. The layers may have a basis weight of from about 15 gsm, from about 35 gsm, from about 50 gsm or from about 80 gsm to 300 gsm or to about 200 gsm. Because the carded web material is a substantially hydrophobic material, it is treated with a surfactant or other process that allows the material to impart a desired level of wettability and hydrophilicity for application in the ADL of the present invention. Treatments such as hydrophilic fiber finishes may be used to make the carded web materials hydrophilic and functional for the present ADL system. The present invention utilizes pre-treated bonded carded web staple fibers such as ESC 236 from FIBERVISION® of Duluth, Ga. and T-295 from INVISTA® of Wichita, Kans.

Layered carded webs of the present invention that are bonded may be, for example, a powder bonded carded web, an infrared bonded carded web, or a through-air bonded carded web. The bonded carded webs can optionally include a mixture or blend of different fibers. The fiber lengths within a selected web may range from about 3 mm to about 60 mm. The present invention differentiates the layers according to the thickness of the fibers as determined by their denier (d) to provide the necessary air permeability and capillary action to drive fluid efficiently in the MD direction and into the deflective layer without an incident of rewet. Thus, the large denier fiber composition layer (120) of the present invention will be greater than about 5 d while the small denier fiber composition layer (130) of the present invention will be below 5 d. The bonded carded web of the present invention can comprise any variety of staple fibers available in the industry, for example, a conjugate sheath/core blend of polyethylene/polyethylene terephthalate (PET/PET) fibers. PE/PET fibers are generally available from TREVIRA® GmbH of Bobingen, Germany. Other fibers may include a conjugate sheath/core blend of polyethylene terephthalate (PET/PET), polyethylene/polypropylene (PE/PP) bicomponent fibers such as those available from FIBERVISIONS® of Duluth, Ga., superabsorbent fibers such as those available from Technical Absorbents of Grimsby, South Humberside DN31 2SS, United Kingdom, and rayon fibers from Kelheim Fibres of Regensburger Str. 109, 93309 Kelheim, Germany. For example, the carded web component of the ADL of the present invention may consist of a large denier fiber composition layer (120) having a basis weight of about 50 gsm made of 50%, 15 d PET/50%, 6 d PE/PP bico above and adjacent to a small denier fiber composition layer (130) having a basis weight of about 15 gsm made of 100%, 3 d PE/PP bico.

The layered carded web layers of the present invention must take insult liquids in at a rate and volume of delivery to avoid top surface pooling or runoff and keep the liquid within the layers. Having a low density of between about 0.1 g/cc and about 0.5 g/cc, the carded web layers also have a naturally low capillary tension which helps to facilitate intake and spreading. The rate of liquid intake is important since it has been found that urination can occur at volumetric rates as high as 15 ml/sec to 20 ml/sec and at velocities as high as 280 cm/sec. Failure to rapidly intake the liquid may result in leakage from areas of the absorbent article. Due to the distinct layers of fibers in the ADL, namely the large denier fibers in the upper layer of the carded web that are separated from the small denier fibers in the lower layer, there is quick intake and little to no rewet to the user. This is distinguishable from what is found in homogeneous blends of fibers that comprise both large and small denier fibers within one layer. The capillary wicking within homogeneous layers allows for fluids to wick in all directions, even back to the top of the layer due to the attraction or affinity for the fluid to move in the direction where small denier fibers are found. The present invention creates a capillary force in the Z-direction towards the absorbent core and a fluid movement in the MD direction such that the fluid is not attracted to the top layer of the ADL where there comprise large denier fibers. At the very least, liquid may deflect and stay within the bottom, small denier fiber layer of the carded web materials until absorbed into the core. The present invention, however, eliminates the desire for the liquid to move entirely to the top layer of the ADL and cause leakage or rewet to a user's skin.

Controlled spreading of the liquid or fluid distribution from an insult is equally important and the intake and controlled spreading objectives of the present invention are achieved by the structure and materials used in the present ADL. Such ADL has an increased level of capillary control in the Z direction due to the deflection layer provided by the fibrous nonwoven layer comprising a meltblown component as discussed herein. The capillary pressure provided by each layer of the carded web materials increases down into the deflection layer and ultimately the absorbent core. Hence, the liquid leaves from the top layer rapidly after insult and is drawn slowly and efficiently into the lower layers. The flow and distribution of liquid must take place at an acceptable rate such that after the initial insult the absorbent system is ready for the next insult. The time between insults can range from just a few minutes to hours, generally depending on the age of the wearer and the type of absorbent article that incorporates the ADL. In order to achieve a controlled movement of fluid, the ADL must have a high capillary tension value. Capillary tension in the ADL is measured simply by the equilibrium wicking of an 8.5 g/ml saline solution. Thus, a successful ADL must have a capillary tension greater than the adjacent layer positioned above (in the Z-direction) and preferably a capillary tension of at least about 15 cm.

Deflection Layer

The deflection layer sits directly below the dual layers of carded web and directly above the absorbent core. The deflection layer is a fibrous nonwoven web wherein at least one component is meltblown. For example, the deflection layer may be all meltblown or a material that contains meltblown along with other components, such as coform. The meltblown component in the deflection layer has an air permeability of from about 45 $ft^3/min/ft^2$, from about 50 $ft^3/min/ft^2$ or from about 75 $ft^3/min/ft^2$ to about 120 $ft^3/min/ft^2$, to about 175 $ft^3/min/ft^2$, or to about 350 $ft^3/min/ft^2$.

Meltblown webs of the present invention may be formed from monocomponent or multicomponent meltblown fibers. Monocomponent fibers are generally formed from a polymer or blend of polymers extruded from a single extruder. Multicomponent fibers are generally formed from two or more polymers (e.g., bicomponent fibers) extruded from separate extruders. The polymers may be arranged in distinct zones across the cross-section of the fibers. The components may be arranged in any desired configuration, such as sheath-core, side-by-side, pie, island-in-the-sea, three island, bull's eye, or various other arrangements known in the art. Various methods for forming multicomponent fibers are described in U.S. Pat. No. 4,789,592 to Taniguchi et al. and U.S. Pat. No. 5,336,552 to Strack et al., U.S. Pat. No. 5,108,820 to Kaneko, et al., U.S. Pat. No. 4,795,668 to Kruege, et al., U.S. Pat. No. 5,382,400 to Pike, et al., U.S. Pat. No. 5,336,552 to Strack, et al., and U.S. Pat. No. 6,200,669 to Marmon, et al. Multicomponent fibers having various irregular shapes may also be formed, such as described in U.S. Pat. No. 5,277,976 to Hogle, et al., U.S. Pat. No. 5,162,074 to Hills, U.S. Pat. No. 5,466,410 to Hills, U.S. Pat. No. 5,069,970 to Largman, et al., and U.S. Pat. No. 5,057,368 to Largman, et al.

Figure 4A:
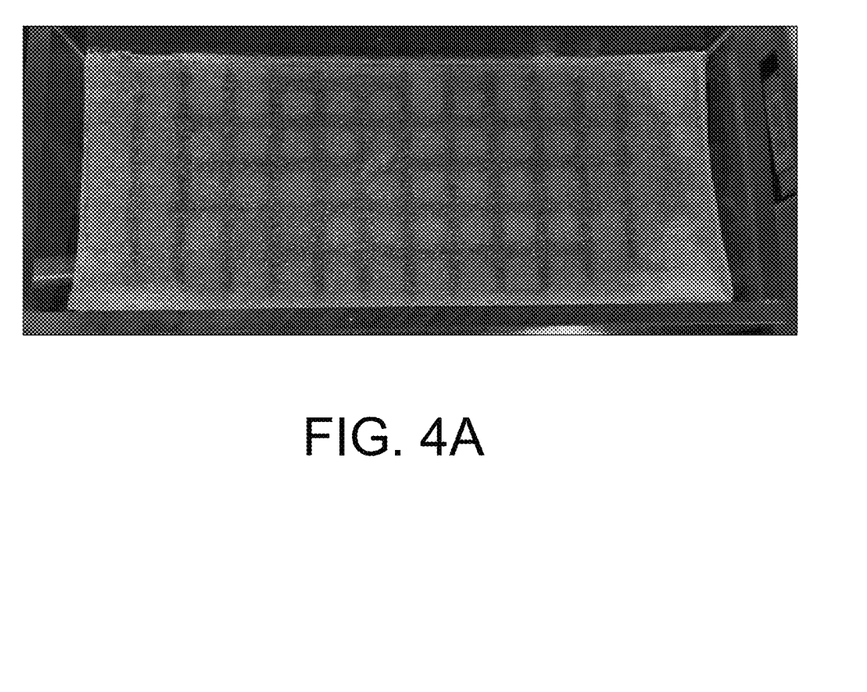
FIG. 4A is a photo of the ADL of the present invention with a basis weight of 95 gsm.

Meltblown materials used for the deflection layer of the present invention are preferably made from a high melt flow polypropylene homopolymer resin or from a polypropylene elastic olefin blend and usually has a fiber diameter of from about 4 microns to about 10 microns. The basis weight of the meltblown materials of the present invention is preferably from about 15 gsm to about 50 gsm. The material may be colored a different color that of the carded web layers or the absorbent core in order to aesthetically distinguish said deflection layer from other layers within the absorbent system. The deflection layer may also be a film such as an apertured film. Although the meltblown material has high surface area fibers, is often made from hydrophobic polymers, and is typically used as a barrier layer, the meltblown material of the present invention is distinguished herein as a deflection layer essential to providing the functioning benefits of the present ADL. Such meltblown is treated to be hydrophilic through the use of a surfactant or a hydrophilic melt additive such as TECHSURF® by Techmer PM, LLC of Rancho Dominguez, Calif. Although treated, low permeability properties are still present within the material to give the desired properties that function as a deflection layer and slow the fluid movement in the Z-direction. This allows the carded web layers that are positioned above to be more efficient in utilizing the full capacity of the ADL. Additionally, the fibers of the carded web layers are oriented in the MD. Thus, the combination of the fiber orientation in the MD and the deflection of the fluid in the Z-direction aid the fluid distribution in order that more of the ADL is used to thereby improve the effectiveness of the entire absorbent system. As shown in FIG. 4A, the inclusion of the deflection layer allows for an enhanced level of wicking such that there is also no localized wet spot typical of other ADL structures such as in FIG. 4B. The fluid moves in the Z direction but also disperses throughout the entirety of the bonded carded web and deflection layers prior to being absorbed by the absorbent core. Thus, the liquid also moves along the MD to utilize the majority of the material as it transfers down into the absorbent core.

To demonstrate and test the fluid distribution of the ADL, such as that shown in FIGS. 4 & 6, approximately 85 ml of fluid was delivered with a calibrated pump to the center of the material at a rate of 15 ml/sec. After 1 minute, the material was weighed and then placed on top of an absorbent core. A weight of about 82.8 g was placed on top of the material and after 1 minute, the material was weighed again. FIGS. 5A and 5B show graphical representations of FIG. 4. The three bars shown for each condition (dry weight, wet weight, desorbed weight) represent the reproducibility in the data. That is, the measurements were taken three times to ensure accuracy. As shown in FIG. 5A, the ADL of the present invention utilizes a majority of the ADL structure for the fluid and holds almost 2× more fluid than a standard ADL structure (FIG. 5B). The structure of the present ADL maximizes distribution of fluid in the MD, temporarily holds a large amount of fluid due to the slow capillary movement created by the deflection layer and then, maximizes the fluid transfer to the absorbent core. In addition to showing that the wet weight is almost twice as much (the ADL retains more fluid), FIG. 5A also shows that the desorbed weight of the ADL of the present invention is lower than the standard desorbed weight. After the ADL is placed onto an absorbent core, the ADL of the present invention is able to desorb more liquid into the absorbent core as a result of the compositional structure. The ADL is able to desorb from about 75%, from about 80% or from about 85% of the fluid compared to a standard ADL which may desorb only about 50%. It is important to note the amount of fluid desorbed into the absorbent core because any fluid that is not desorbed is left for possible rewetting and leakage issues. Having as little desorbed fluid in the ADL as possible helps to minimize leakage issues. With an average of about 20% or less of the fluid remaining, the ADL of the present invention shows a significant improvement over standard ADLs used within absorbent systems.

The deflection layer of the present invention may also be a coform web, which contains meltblown. Coform is a considerable deflection layer material since it contains a meltblown component as well as other components that assist in fluid absorption such as fluff pulp. Although an alternative fluff material such as airlaid can be appreciated, the present invention focuses on materials that contain meltblown such as coform since airlaid does not present the acceptable size of fibers to create the appropriate capillary flow of the liquid in the MD. Thus, it is preferred that coform is selected over the use of airlaid. Additionally, since coform comprises fluff pulp fibers, the absorbent capacity may aid in the functioning of the absorbent core. Moreover, if a pulpless core is used as the absorbent core, coform may provide an alternative means for additional absorbency.

The coform web useful as the deflection layer in the present invention can generally be made by a process in which at least one meltblown die head (e.g., two) is arranged near a chute through which the absorbent material, such as pulp, is added while the web forms. Some examples of such coform techniques are disclosed in U.S. Pat. No. 4,100,324 to Anderson, et al.; U.S. Pat. No. 5,350,624 to Georger, et al.; and U.S. Pat. No. 5,508,102 to Georger, et al.

Any absorbent material may generally be employed in the coform web, such as absorbent fibers, particles, pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Exemplary commercially available pulp fibers suitable for the present invention include those available from Weyerhaeuser Co. of Federal Way, Wash. under the designation WEYCO CF-405®; GOLDEN ISL ES® 4824 from GP CELLULOSE® of Brunswick, Ga. The pulp may also be POROSANIER® treated pulp such as that made commercially available from Rayonier, Inc. of Jacksonville, Fla. In certain instances, *eucalyptus* fibers may be particularly desired to increase the softness of the web. *Eucalyptus* fibers can also increase the opacity, change the pore structure of the web, or increase the wicking ability. Moreover, if desired, secondary fibers obtained from recycled materials may be used, such as fiber pulp from sources such as, for example, newsprint, reclaimed paperboard, and office waste. Further, other natural fibers can also be used in the present invention, such as abaca, sabai grass, milkweed floss, pineapple leaf, and the like. In addition, in some instances, synthetic fibers can also be utilized.

Air Permeability

Figure 6A:
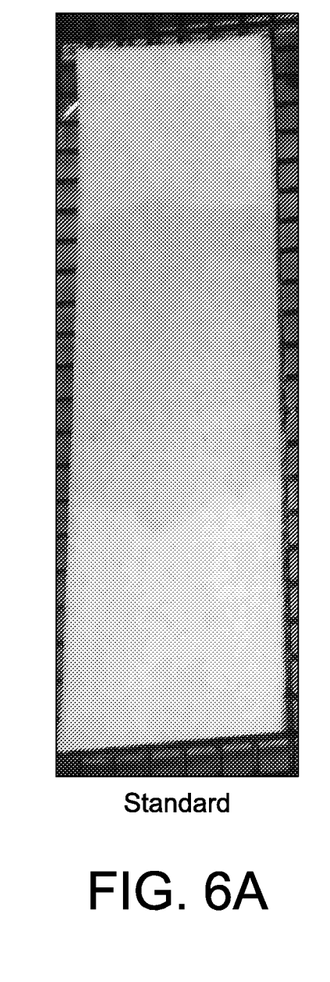
FIG. 6A shows a standard surge material that has been insulted with 85 ml of colored saline at a rate of about 15 ml/sec.
Figure 6B:
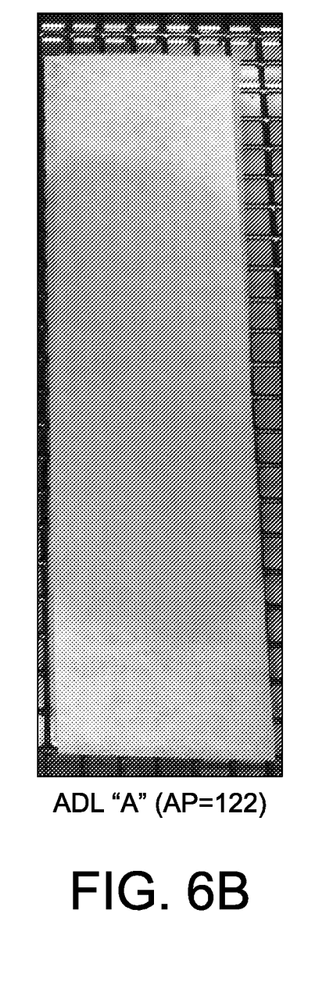
FIG. 6B shows the ADL of the present invention that has been insulted with 85 ml of colored saline at a rate of about 15 ml/sec and wherein the air permeability is 122 ft$^3$/min/ft$^2$.
Figure 6C:
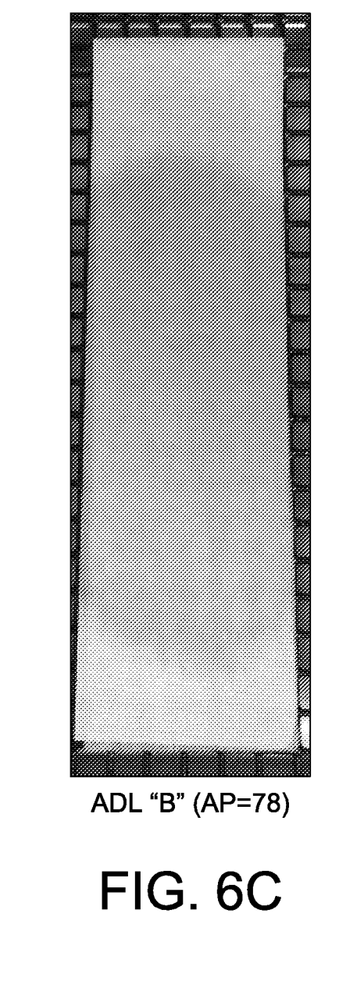
FIG. 6C shows the ADL of the present invention that has been insulted with 85 ml of colored saline at a rate of about 15 ml/sec and wherein the air permeability is 78 ft$^3$/min/ft$^2$.
Figure 6D:
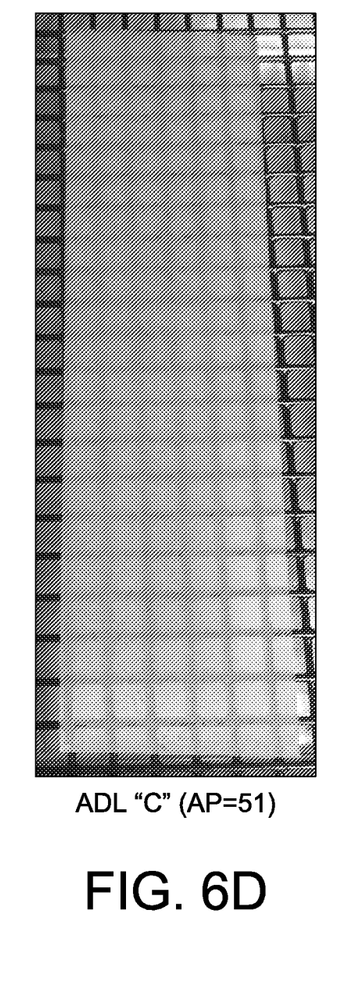
FIG. 6D shows the ADL of the present invention that has been insulted with 85 ml of colored saline at a rate of about 15 ml/sec and wherein the air permeability is 51 ft$^3$/min/ft$^2$.
Figure 7:
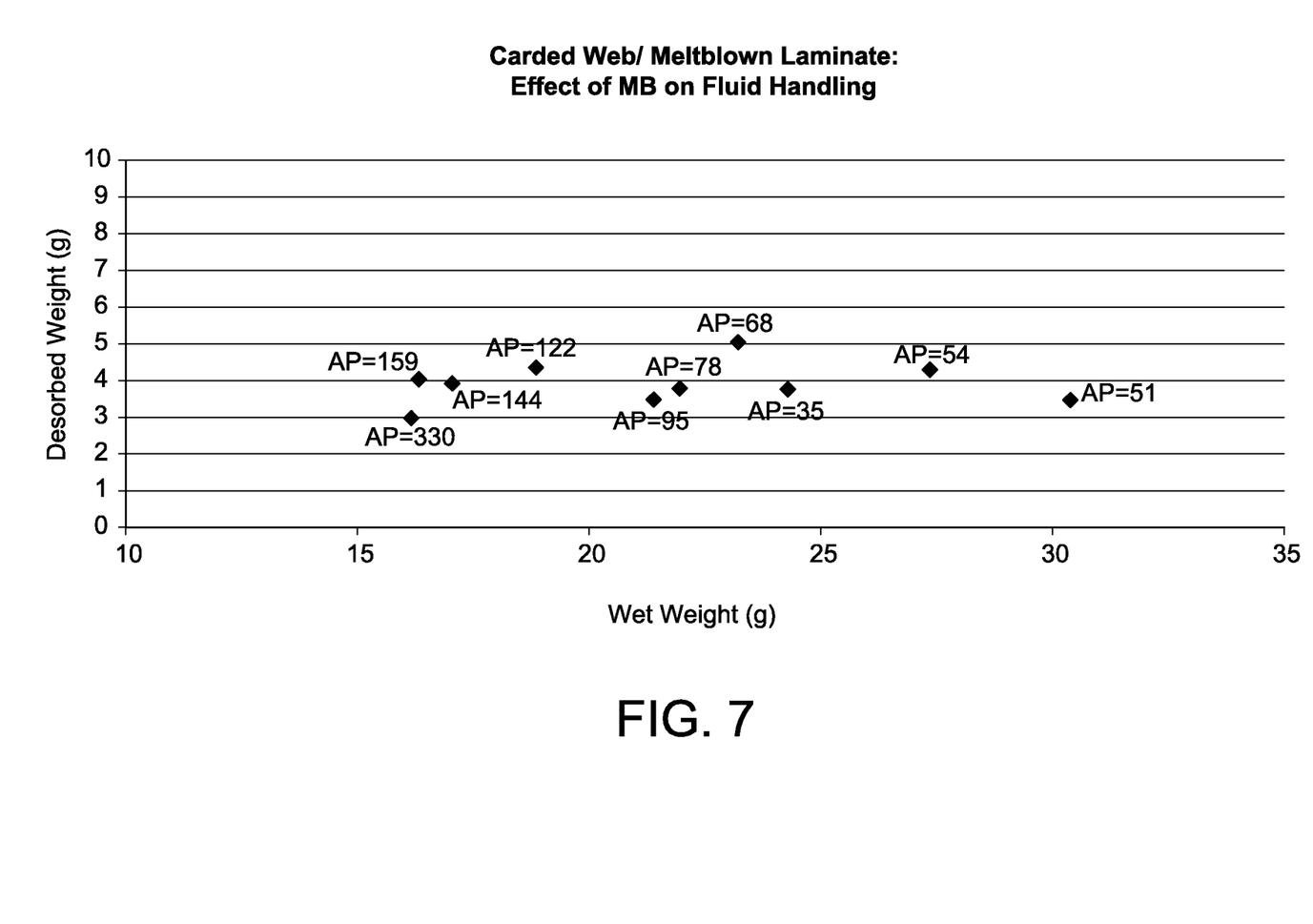
FIG. 7 gives a graphical illustration of the effect of fluid handling on the ADL of the present invention.

Air permeability can be used as an indicator of pore structure of the ADL. Pore structure plays a significant factor in the present ADL as it helps to control the rate at which the liquid flows in order to assure that more of the materials within the ADL are being used. The air permeability is determined by the Standard Method of Test for Air Permeability of Textile Fabrics, also known as the Frazier Air Porosity Test or ASTM D737. Air permeability is the rate of air flow through a material under a differential pressure between the two fabric surfaces and is expressed in cubic feet of air per minute per square foot ($ft^3/min/ft^2$) of fabric at a stated pressure differential between the two surfaces of the fabric. Measurements found herein were made at a differential water gauge pressure of 125 Pascals. MD core spreading is shown to be improved with the structure of the present ADL as it is shown that a lower air permeability helps to achieve the objective of the invention since there is enhanced distribution of fluid in the MD. FIGS. 6A-6D shows from left to right a standard surge material along with the ADL of the present invention wherein each sample decreases in air permeability. The structure of the ADL of the present invention alone allows for the material to be utilized more efficiently. When the air permeability is also factored in and adjusted, this adds a greater level of efficiency to the invention. The air permeability of the meltblown component in the deflection layer of the present invention may be from about 45 $ft^3/min/ft^2$, from about 50 $ft^3/min/ft^2$ or from about 75 $ft^3/min/ft^2$ to about 120 $ft^3/min/ft^2$, to about 175 $ft^3/min/ft^2$, or to about 350 $ft^3/min/ft^2$. As shown, as air permeability decreases, the efficiency of the ADL increases. As shown in FIGS. 6B-6D, as air permeability decreases, fluid distribution in the MD increases thereby increasing the overall efficiency of the ADL. FIG. 7 gives a graphical illustration of the effect of fluid handling on the ADL of the present invention. As shown, the lower air permeability samples hold more fluid. Although the desorbed weight is independent of air permeability, all of the samples show a low desorbed weight of about 3 to about 5 grams. Thus, while the ADL is able to handle more fluid primarily due to the presence of the deflection layer, it also is able to transfer most of the fluid into the absorbent core and leave very little fluid in the ADL for rewet or leaks.

Absorbent Articles

The ADL of the present invention is useful in an array of absorbent articles, particularly disposable absorbent articles including, but not limited to baby and child care products such as diapers and training pants, incontinence products, feminine care products such as sanitary napkins, and the like, surgical bandages, sponges, and the like. Due to the enhanced fluid intake and distribution materials, free fluid is minimized particularly against low load leakage.

Materials and processes suitable for forming such absorbent articles are well known to those skilled in the art. Absorbent articles may include a substantially liquid-impermeable layer (e.g., outer cover), a liquid-permeable layer (e.g., bodyside liner), and an absorbent core. An absorbent article useful for including the present invention may also have other components such as an elastic waistband, leg cuff/gasketing (leg band), stretchable ear, side panel, outer cover, or any other component in which elastic properties are desirable. Various embodiments of an absorbent article, particularly a training pant that may be formed utilizing the ADL of the present invention are described in U.S. Pat. No. 8,343,127 to Dimitrijevs, et al. or U.S. Pat. No. 4,940,464 to Van Gompel et al. Other embodiments that may employ an absorbent core similar to that which could be used with the ADL of the present invention may be found in absorbent articles similar to those disclosed in U.S. Pat. No. 7,938,813 to Wang, et al.; U.S. Pat. No. 5,853,402 to Faulks et al.; and U.S. Pat. No. 6,706,945 to Melius.

Absorbent articles typically include a bodyside liner which is generally used to help isolate the wearer's skin from liquids entering into the ADL of the present invention. For example, the liner presents a body facing surface that is typically compliant, soft feeling, and non-irritating to the wearer's skin. Typically, the liner is also less hydrophilic than the absorbent core so that its surface remains relatively dry to the wearer. The liner may be liquid-permeable to permit liquid to readily penetrate through its thickness. Exemplary liner constructions are described in U.S. Pat. No. 5,192,606 to Proxmire, et al.; U.S. Pat. No. 5,702,377 to Collier, I V, et al.; U.S. Pat. No. 5,931,823 to Stokes, et al.; U.S. Pat. No. 6,060,638 to Paul, et al.; and U.S. Pat. No. 6,150,002 to Varona, as well as U.S. Patent Application Publication Nos. 2004/0102750 to Jameson; 2005/0054255 to Morman, et al.; and 2005/0059941 to Baldwin, et al.

The outer cover is typically formed from a material that is substantially impermeable to liquids. For example, the outer cover may be formed from a thin plastic film or other flexible liquid-impermeable material such as a polyethylene film. The film may be impermeable to liquids, but permeable to gases and water vapor (i.e., "breathable"). This permits vapors to escape from the absorbent core, but still prevents liquid exudates from passing through the outer cover.

An absorbent article utilizing the ADL of the present invention may also include a pair of side panels (or ears) that extend from the side edges of the absorbent article into one of the waist regions. The side panels may be integrally formed with a selected absorbent article component. For example, the side panels may be integrally formed with the outer cover or from the material employed to provide the top surface. In alternative configurations, the side panels may be provided by members connected and assembled to the outer cover, the top surface, between the outer cover and top surface, or in various other configurations. If desired, the side panels may be elasticized or otherwise rendered elastomeric by use of the elastic nonwoven composite of the present invention. Examples of absorbent articles that include elasticized side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries.

As is typical, an absorbent article embodying the ADL of the present invention may also include a pair of containment flaps that are configured to provide a barrier and to contain the lateral flow of body exudates. The containment flaps may be located along the laterally opposed side edges of the bodyside liner adjacent the side edges of the ADL and absorbent core. The containment flaps may extend longitudinally along the entire length of the absorbent core, or may only extend partially along the length of the absorbent core. When the containment flaps are shorter in length than the absorbent core, they may be selectively positioned anywhere along the side edges of diaper in a crotch region. In one embodiment, the containment flaps extend along the entire length of the absorbent core to better contain the body exudates. Such containment flaps are generally well known to those skilled in the art. For example, suitable constructions and arrangements for the containment flaps are described in U.S. Pat. No. 4,704,116 to Enloe.

To provide improved fit and to help reduce leakage of body exudates, the absorbent article may be elasticized with suitable elastic members, as further explained below. For example, the absorbent article may include leg elastics constructed to operably tension the side margins of the diaper to provide elasticized leg bands which can closely fit around the legs of the wearer to reduce leakage and provide improved comfort and appearance. Waist elastics may also be employed to elasticize the end margins of the absorbent article to provide elasticized waistbands. The waist elastics are configured to provide a resilient, comfortably close fit around the waist of the wearer. The elastic nonwoven composite of the present invention is suitable for use as the leg elastics and waist elastics. Exemplary of such materials are laminate sheets that either comprise or are adhered to the outer cover so that elastic constrictive forces are imparted thereto.

The various regions and/or components of the absorbent article may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the outer cover and bodyside liner are assembled to each other and to the absorbent core using an adhesive. Alternatively, the absorbent core may be connected to the outer cover using conventional fasteners, such as buttons, hook and loop type fasteners, adhesive tape fasteners, and so forth. Similarly, other absorbent article components, such as the leg elastic members, waist elastic members and sometimes even fasteners, may also be assembled into the absorbent article using any attachment mechanism.

Although various configurations of an absorbent article have been described above, it should be understood that other absorbent article configurations are also included within the scope of the present invention. In addition, any absorbent article may be formed in accordance with the present invention, including, but not limited to, personal care absorbent articles, such as training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth. Several examples of such absorbent articles are described in U.S. Pat. No. 5,649,916 to DiPalma, et al.; U.S. Pat. No. 6,110,158 to Kielpikowski; U.S. Pat. No. 6,663,611 to Blaney, et al. Still other suitable articles are described in U.S. Patent Application Publication No. 2004/0060112 A1 to Fell et al., as well as U.S. Pat. No. 4,886,512 to Damico et al.; U.S. Pat. No. 5,558,659 to Sherrod et al.; U.S. Pat. No. 6,888,044 to Fell et al.; and U.S. Pat. No. 6,511,465 to Freiburger et al. The present invention is particularly beneficial to absorbent articles having a front panel, two side panels, and a back panel.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Example 1

A fluid handling test was performed for the ADL of the present invention versus a standard ADL in order to evaluate the fluid distribution and transfer. The ADL of the present invention comprised a dual layered through air bonded carded web (TABCW) with a meltblown deflection layer. The top layer of the dual layered TABCW on the body-facing side was about 50 gsm in basis weight and contained a 50/50 large denier fiber mix of 16 d PET and 6 d PE/PP bico fibers. The bottom layer of the dual layered TABCW was about 15 gsm in basis weight and contained a small denier fiber of 100% of 3 d PE/PP bico fibers. The dual layered TABCW was in the form of one layer as both separate layers had been through air bonded together in the process. The meltblown deflection layer was about 26 gsm in basis weight and contained 82% Basell 650X polypropylene, 15% SCC 84148 (a compounded blend of 85% Exxon VMX 6202FL, 12.3% Exxon 3155, and 2.7% CR10PX2 Polyvel peroxide concentrate), and 3% Techsurf. The air permeability of this meltblown deflection layer was measured at 51 ft$^3$/min/ft$^2$. It was placed on the 3 d PE/PP bico fiber side of the dual layered TABCW. The meltblown deflection layer and the TABCW were heat sealed together at the edges. The control ADL used as a comparative herein is a surge material comprising a homogeneous blend of fibers (35% 6 d PE/PP bico, 35% 1.5 d PE/PP Bico, and 30% 6 d PET).

Figure 4B:
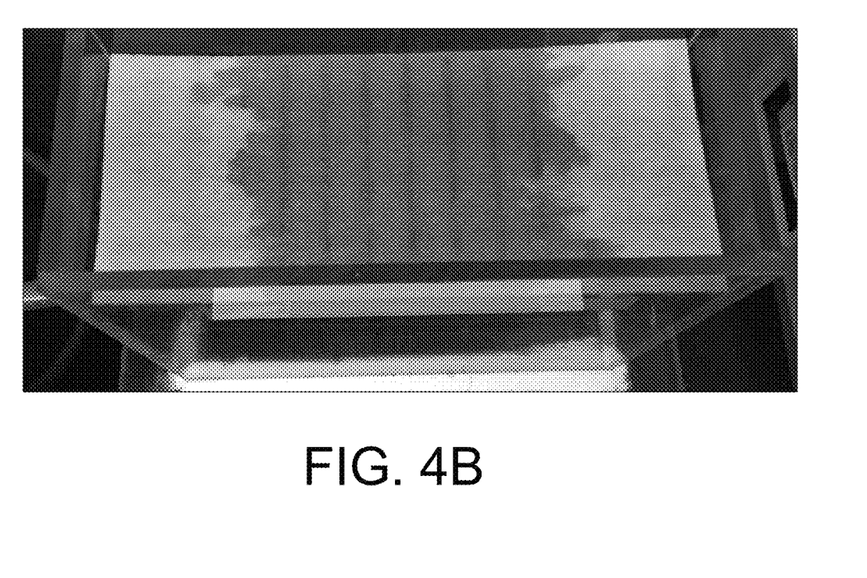
FIG. 4B is a photo of a standard ADL which includes a homogeneous blend of fibers (35%, 6 d PE/PP bico, 35%, 1.5 d PE/PP Bico, 30%, 6 d PET), with a basis weight of 100 gsm.
Figure 5A:
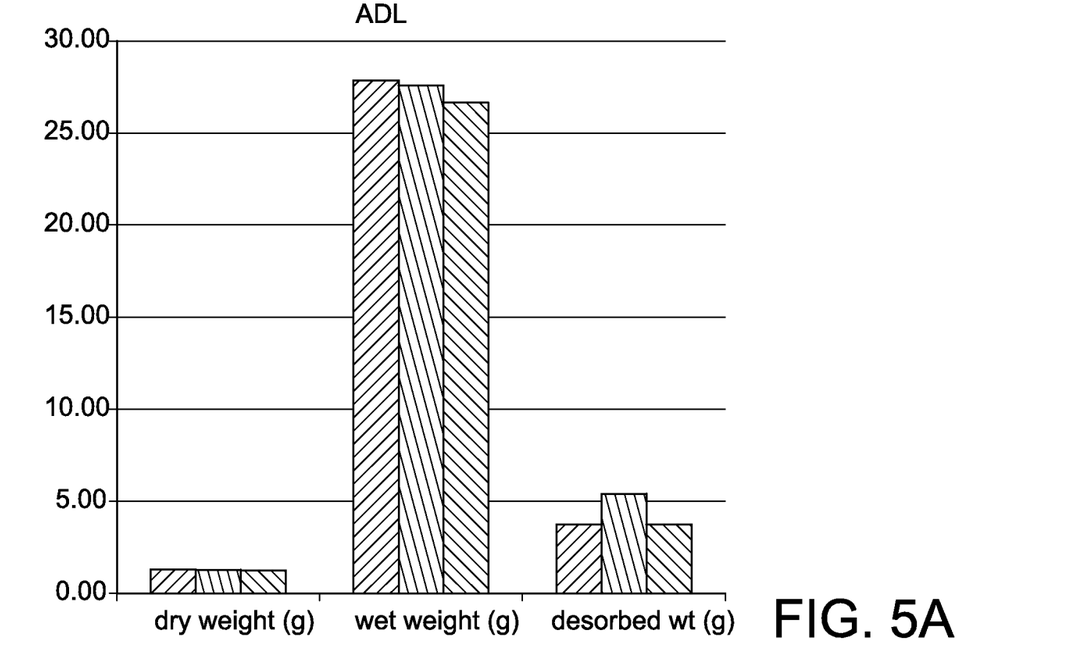
FIG. 5A shows a graphical illustration of the intake and desorbed weights of the present invention.
Figure 5B:
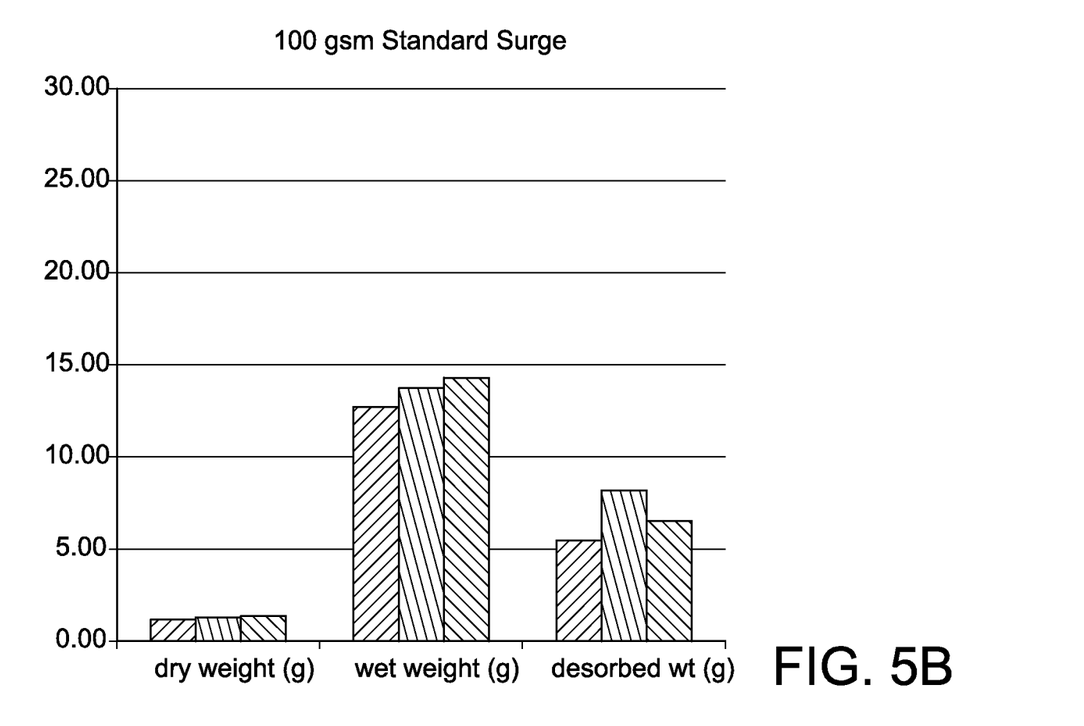
FIG. 5B shows a graphical illustration of the intake and desorbed weights of a standard ADL.

The procedure for the fluid handling test involved placing a sample of the ADL (3-inch CD×7-inch MD) on a flat wire mesh (3-inch CD×7-inch MD) that was suspended above the floor and inside of a plastic support (shown in FIGS. 4A-B). The top of the plastic support was open to allow the fluid to be delivered to the center of the sample of the ADL. The fluid delivery occurred from a nozzle that was positioned perpendicular to and about 0.25-inch above the center of the 3" by 7" inch sample. The flat wire mesh that supported the sample of the ADL rested about 1 inch below the top of the walls that formed the rectangular plastic support. Therefore, the fluid could only move within the material or through it. The fluid was room temperature saline that was colored blue with a dye in order that it could be easily seen. The fluid volume delivered to the center of each sample of the ADL was about 85 ml and the rate was about 15 ml/sec. The volume and rate of fluid were delivered from a tube and calibrated pump. When the pump had completed the 85 ml delivery of fluid to the ADL, a timer was started and after 1 minute, the fluid insulted ADL was carefully lifted from the wire support and weighed. This weight minus any excess fluid left behind in the weighing dish was recorded as "wet weight" (as illustrated in FIGS. 5A-B). The fluid insulted ADL was then placed on an absorbent core that contained 70% superabsorbent/30% fluff pulp and an 82.8 gram weight (rectangular plastic bag (1 inch width by 6 inch length) that contained BBs) was placed on top and center of the 3" by 7" sample. After 1 minute, the weight was removed and the ADL and absorbent core were both weighed. The weight of the ADL after this step is referred as "desorbed weight" (as illustrated in FIGS. 5A-B).

Results of the fluid handling test can be seen demonstratively in FIGS. 4A-B and graphically in FIGS. 5A-B. FIG. 4A shows a photograph of the inventive ADL and FIG. 4B shows a photograph of a standard ADL wherein both samples are shown 1 minute after the pump had delivered the 85 ml of fluid. FIG. 5A graphs the amount of fluid held by the ADL (wet weight), followed by the amount of fluid left in the ADL after desorption to the underlying absorbent core (desorbed weight).

The ADL of the present invention is exemplified with the following characteristics: a top layer comprising a large denier fiber composition layer having a basis weight of about 50 gsm made of 50%, 15 d PET/50%, 6 d PE/PP bico, a second layer comprising a small denier fiber composition layer having a basis weight of about 15 gsm made of 100%, 3 d PE/PP bico with a deflection layer of a meltblown web.

Note that the ADL of the present invention shown in FIG. 4A utilizes a majority of the ADL structure for temporary storage of fluid compared to the standard ADL shown in FIG. 4B. Furthermore, FIG. 5A shows the ADL of the present invention as holding almost 2× more fluid than the standard ADL structure, even though the basis weight is essentially the same for both structures (i.e. 90 gsm to 100 gsm). Also, rather unexpected, the ADL of the present invention is very effective at transferring the fluid to the underlying absorbent core, as it contains less fluid after the desorption step than the standard ADL (FIG. 5B). In summary, the fluid handling test shows that the structure of the present ADL maximizes spreading of fluid in the MD, temporarily holds a large amount of fluid due to the slow capillary movement of fluid in the Z direction (due to the deflection layer) and then, maximizes the fluid transfer to the absorbent core, all without any leaks.

Example 2

Figure 3:
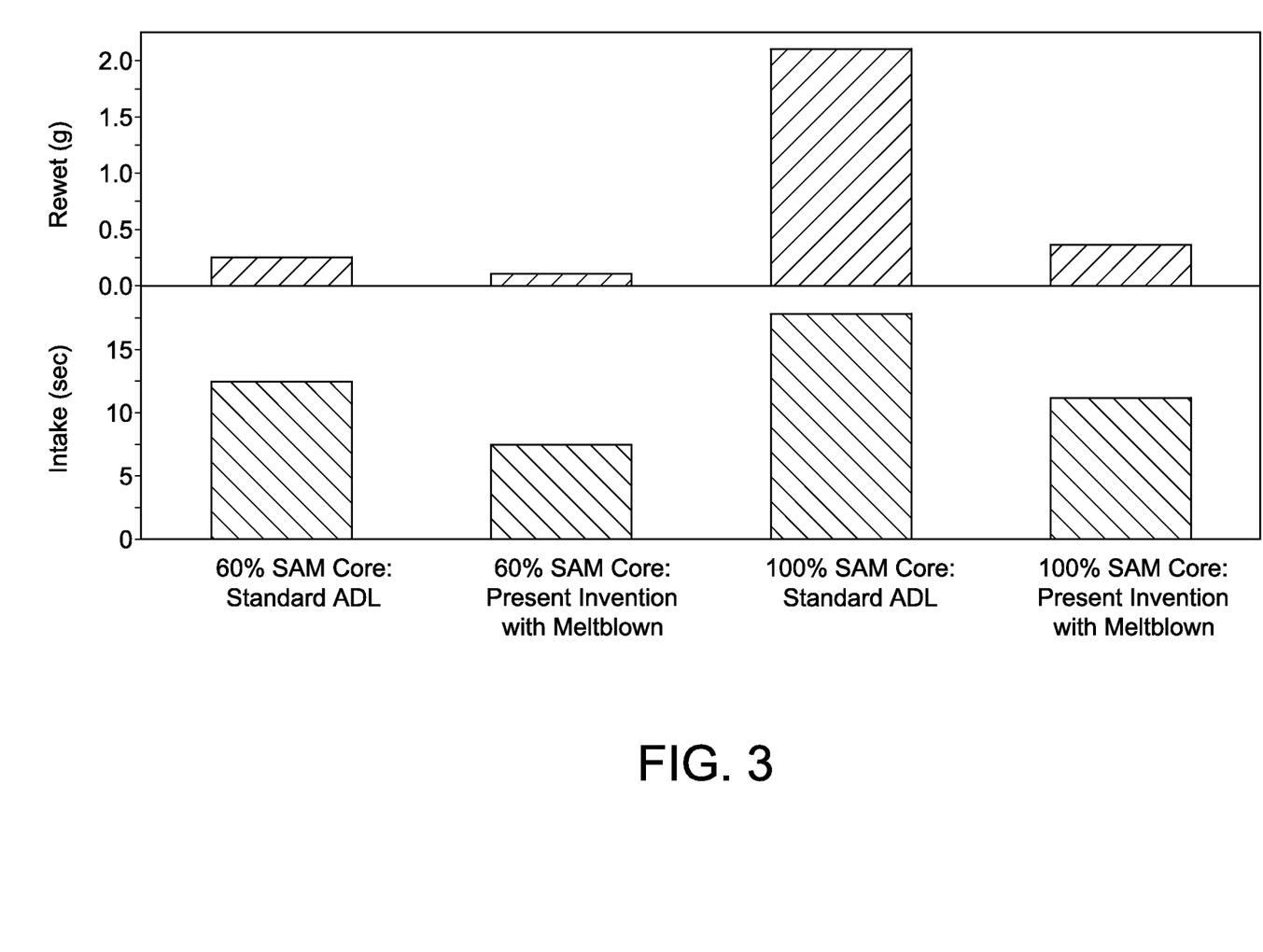
FIG. 3 is a graphical representation of the intake and rewet benefits of the present invention with high superabsorbent cores.

A second fluid handling test was performed for the ADL of the present invention versus a standard ADL to evaluate the intake rate of fluid and amount of fluid rewet. The characteristics of the ADL of the present invention and standard ADL were the same as that which was described in Example 1. For this test, a sample of the ADL was placed on top of an absorbent core. The ADL and absorbent core were both about 5 inches in width and about 10 inches in length. A rectangular plastic plate also about 5 inches in width and about 10 inches in length having a circular opening about 1 inch in diameter that is attached to a cylinder about 10 inches high was then placed on top of the ADL. The fluid was poured into this cylinder and the intake time was measured as the time it takes for the fluid to drain from the cylinder into the ADL. For this test, 85 ml of colored saline at room temperature was used as the fluid. As soon as the fluid had completely drained into the ADL, the rectangular plastic plate was removed and a piece of pulp board also about 5 inches in width by about 10 inches in length was placed on top of the ADL. The rectangular plastic plate was then placed on top of the pulp board. After 2 minutes, the pulp board was retrieved and weighed. Any increase in weight for the pulp board is considered fluid rewet. FIG. 3 shows the intake rate and rewet data for the ADL of the present invention wherein the deflection layer is meltblown. Also shown in FIG. 3 is the intake and rewet data for the standard ADL for two different absorbent cores: a 60% superabsorbent (SAM)/40% fluff pulp core and a 100% SAM core. It can be seen that the ADL of the present invention is especially effective for the 100% SAM core, providing both faster fluid intake and much lower fluid rewet when compared to the standard ADL. This example clearly shows the benefit of the dual layered bonded carded web with a meltblown deflection layer for providing improved fluid handling properties, particularly for absorbent products with absorbent cores that contain high levels of superabsorbent.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven acquisition distribution layer comprising: a) layered carded webs having at least a first layer and a second layer; and b) a deflection layer; wherein said first layer of said layered carded web comprises a carded web with high denier fibers wherein the denier is greater than about 5 d and a second layer of said layered carded web comprising a carded web with low denier fibers wherein the denier is less than about 5 d and is positioned just below and in direct contact with said first layer; and wherein said deflection layer comprises a fibrous nonwoven web wherein the fibrous nonwoven web has at least one component comprising meltblown, said meltblown having a basis weight of from about 15 gsm to about 50 gsm and having an air permeability of from about 45 $ft^3/min/ft^2$ to about 350 $ft^3/min/ft^2$; and wherein the deflection layer is positioned just below and in direct contact with said second layer of said layered carded web.

2. The nonwoven acquisition distribution layer of claim 1 wherein the deflection layer is a coform web.

3. An absorbent article comprising an absorbent system wherein the absorbent system comprises the nonwoven acquisition distribution layer of claim 1 positioned adjacent to and above an absorbent core.

4. The nonwoven acquisition distribution layer of claim 1 wherein the layered carded web is bonded by a bonding means selected from powder bonding, infrared bonding, or through-air bonding.

5. The nonwoven acquisition distribution layer of claim 1 wherein the layered carded web includes at least one additional layer of a carded web material.

6. The nonwoven acquisition distribution layer of claim 1 wherein said first layer of said layered carded web has a basis weight of about 50 gsm, comprising about 50% PET with 15 denier and about 50% PE/PP bico with 6 denier and wherein said second layer of said layered carded web has a basis weight of about 15 gsm, comprising about 100% PE/PP bico with 3 denier.

7. The nonwoven acquisition distribution layer of claim 6 wherein the deflection layer is a coform web.

* * * * *